United States Patent [19]
Seid

[11] Patent Number: 4,742,578
[45] Date of Patent: May 10, 1988

[54] PENETRATION-RESISTANT SURGICAL GLOVE

[76] Inventor: Arnold S. Seid, 427 16th St., Santa Monica, Calif. 90402

[21] Appl. No.: 803,170

[22] Filed: Dec. 2, 1985

[51] Int. Cl.$^4$ .................... A41D 13/10; A41D 19/00
[52] U.S. Cl. ............................... 2/2.5; 2/16; 2/167; 2/168
[58] Field of Search ............... 2/161 R, 159, 164, 168, 2/167, 169, 163, 2.5, 16, 20, 21

[56] References Cited

U.S. PATENT DOCUMENTS

| | | | |
|---|---|---|---|
| 2,058,221 | 10/1935 | Ferguson . | |
| 2,873,450 | 2/1959 | Brodeur, Jr. | 2/168 X |
| 2,907,046 | 10/1959 | Scherr | 2/159 |
| 3,110,035 | 11/1959 | La Hue . | |
| 3,633,216 | 1/1972 | Schonholtz | 2/168 |
| 3,883,898 | 5/1975 | Byrnes, Sr. . | |
| 3,945,049 | 3/1976 | Barlow | 2/169 |
| 4,004,295 | 1/1977 | Byrnes, Sr. | 2/161 R |
| 4,084,269 | 4/1978 | Anfelt | 2/163 |
| 4,214,321 | 7/1980 | Nuwayser . | |
| 4,218,779 | 8/1980 | Hart et al. | 2/168 |
| 4,283,244 | 8/1981 | Hashmi | 2/167 X |
| 4,329,312 | 5/1982 | Ganz | 2/168 X |
| 4,371,988 | 2/1983 | Berend | 2/167 |
| 4,382,301 | 5/1983 | Hightower, Jr. | 2/2.5 X |
| 4,526,828 | 7/1985 | Fogt et al. | 2/16 X |

FOREIGN PATENT DOCUMENTS

| | | | |
|---|---|---|---|
| 1034114 | 7/1958 | Fed. Rep. of Germany | 2/168 |
| 1514101 | 1/1968 | France | 2/168 |
| 488809 | 7/1938 | United Kingdom | 2/168 |
| 522683 | 6/1940 | United Kingdom | 2/168 |

Primary Examiner—Stephen Marcus
Assistant Examiner—T. Graveline
Attorney, Agent, or Firm—B. F. Spencer

[57] ABSTRACT

A penetration-resistant surgical glove is disclosed which consists of a thin latex of synthetic rubber foundation glove having a front surface overlay of thin, pliable and limp material composed of a large number of tightly interlaced fibers or filaments of high strength adhesively attached to the face or palmar surface of the foundation glove. The surface overlay of thin, pliable and limp material is shaped to conform to the thumb, fingers and palm of the foundation glove and serves to prevent penetration of the glove by a sharp object. The foundation glove with its protective overlay of penetration-resistant material may be provided with an overcoat of rubber in the form of a second glove, as by dipping in liquid latex, drying and vulcanizing in the conventional manner. The over-coat of latex rubber provides a hermetic seal over the surface of the foundation glove and its protective overlay. Any rupture or penetration of the hermetic seal occurring during the course of an operation which enables fluids to reach the protective overlay causes a visible staining of the overlay material, thereby providing an indication that such a rupture or penetration has occurred.

8 Claims, 1 Drawing Sheet

PENETRATION-RESISTANT SURGICAL GLOVE

BACKGROUND OF THE INVENTION

The present invention relates to surgical appliances and, in particular, to surgical gloves designed to resist penetration by sharp needles or instruments.

The conventional surgical glove is composed of extremely thin latex or synthetic rubber designed to fit tightly and closely over the surgeon's hand, thereby providing a maximum of tactile sensitivity and ease of manipulation of the thumb and fingers. The glove serves as a protective shield to prevent the passage of contamination either from the hands of the surgeon to the patient or from the wound of the patient to the surgeon. While the thickness of surgical gloves may vary from one type or manufacture to another, the orthopedic surgeon's glove being composed of thicker latex, all are susceptible to puncture or rupture during the course of an operation.

In those cases where the surgeon is particularly concerned with glove puncture, he may employ the practice of double gloving; i.e., the wearing of two pairs of gloves. The protection afforded by this practice is, however, of minimum value providing, at most, only twice the protection of a single glove.

While attempts at solving the problems of rupture and penetration have included double dipping in liquid latex to increase the thickness of the glove, such attempts specifically proposing an increase in the thickness of the thumb and forefinger portions of the glove, the problem persists.

The present invention is directed to an improved surgical glove that is a combination of latex rubber and a thin, pliable and limp overlay of material composed of tightly interlaced fibers of filaments of high strength adhesively attached or bonded to the palmar or front face of the glove. The improved glove provides an appreciable improvement in the resistance to rupture and penetration, such as caused by sharp instruments, while retaining, to a large extent, the feel and tactile sensitivity of the conventional surgical glove.

Accordingly, the principal object of the present invention is to provide an improved penetration-resistant surgical glove.

Another object of the invention is to provide a thin and pliable surgical glove reenforced in the palmar or front surface area with a tightly interwoven, penetration-resistant material to minimize the risks of puncture or rupture.

A further object is to provide a thin, pliable and lightweight reenforced surgical glove having a touch and feel similar to that of conventional latex surgical gloves.

An additional object is to provide a surgical glove providing increased protection to both physician and patient from exposure to contamination.

Still another object is to provide a surgical glove designed to reveal, upon visual inspection, that a rupture or penetration has occurred.

The above objects of and the brief introduction to the present invention will be more fully understood, and further objects and advantages will become apparent, from a study of the following detailed description in connection with the drawings.

BRIEF DESCRIPTIONS OF THE DRAWINGS

DESCRIPTION OF THE INVENTION

Figure 1:
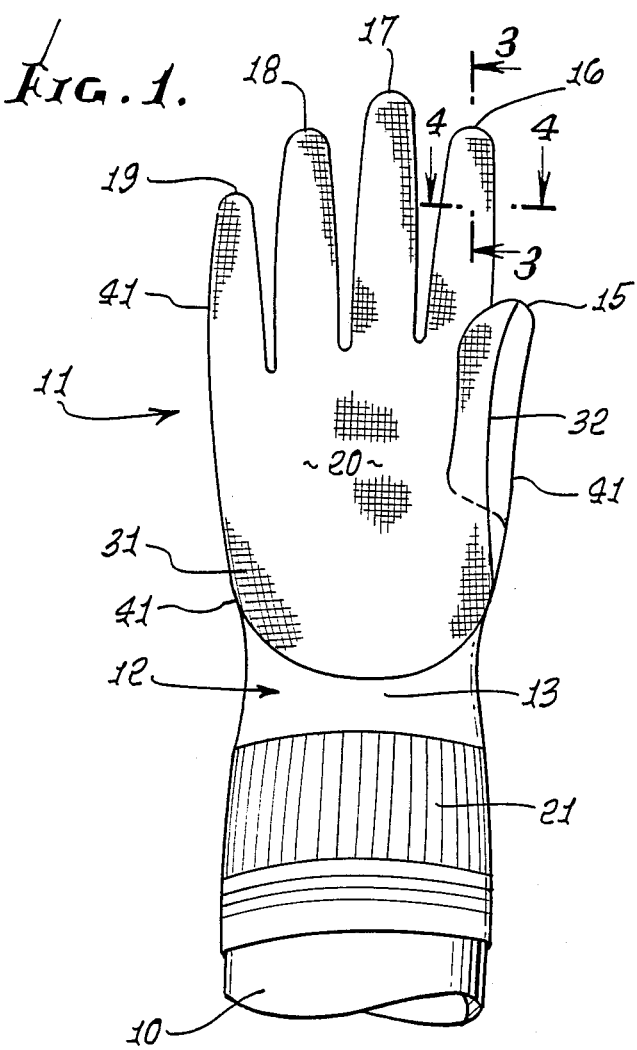
FIG. 1 is a front or palmar view of the preferred embodiment of the penetration-resistant glove of the invention as it appears upon a conventional porcelain form of the human hand.

Referring to FIG. 1, the penetration-resistant glove 11 of the invention is shown situated upon a conventional hollow porcelain form 10 in the shape of the human hand. Hollow porcelain from 10 provides a base or foundation upon which glove 11 may be manufactured.

Fitted upon porcelain form 10 and in physical contact therewith is a first or foundation surgical glove 12 composed of thin, resilient and elastic material, such as latex or synthetic rubber. Foundation glove 12 has a front face or palmar surface 13, a rear surface 14, and includes thumb portion 15, finger portions 16–19, and palm portion 20, as shown. Glove 12 also includes cuff portion 21 for surrounding the wrist.

Foundation glove 12 may be pre-manufactured and manually placed or fitted upon porcelain form 10, or it may be manufactured directly upon form 10 by the conventional process of dipping the form in liquid latex, withdrawing, drying and vulcanizing. Glove 12 may have a thickness of three- to five-thousandths of an inch.

Attached to the front face or palmar surface 13 of foundation glove 12 is a thin overlay of penetration-resistant cloth material 31, pre-cut in the shape of the thumb 15, fingers 16–19 and palm portion 20 of glove 12. Overlay material 31, shown as shaded or cross-hatched lines, is composed of a very large number of tightly interlaced fibers of filaments of high tensile strength, as will be more fully described hereinbelow.

Figure 4:
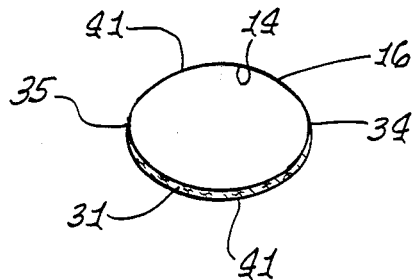
FIG. 4 is an enlarged cross-sectional view of the index finger portion of the glove of FIG. 1 taken along the line 4—4.

Overlay material 31 is pre-cut from the thin, penetrationresistant cloth material and is sized somewhat wider than thumb 15, fingers 16–19 and palm portion 20 of glove 12. This wider sizing enables overlay material 31 to be wrapped partially about the left and right sides of thumb 15 and fingers 16–19, as illustrated in FIGS. 1, 2 and 4.

To attach overlay material 31 to the front face 13 of glove 12, a thin, surface coat of adhesive or contact cement is applied evenly to the rear surface of the material, as by spraying or spreading. This thin coat of adhesive may be applied to the rear surface after overlay material 31 has been pre-cut, or it may be applied to the cloth material while still in its flat cloth form, the applied adhesive coat being protected by a non-adherent film or backing.

The pre-cut, shaped, adhesively coated overlay material 31 is carefully aligned with the matching front surface of thumb 15, fingers 16–19, and palm portion 20 of glove 12 and attached thereto. Proper alignment assures that the edges of overlay material 31 will extend partially about thumb 15 and fingers 16–19 to the middle of each side of thumb 15 and fingers 16–19, as may be seen in FIGS. 1, 2 and 4.

Figure 2:
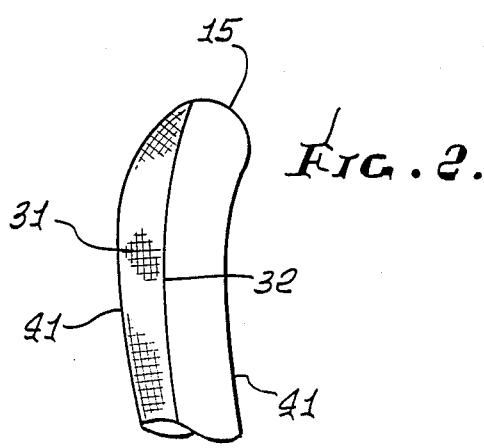
FIG. 2 is an enlarged side view of the thumb portion of the glove of FIG. 1, illustrating the partial wrap-around of the penetration-resistant material.

The enlarged side view of FIG. 2 shows the edge 32 of overlay material 31 positioned and affixed along the middle of the right side of the thumb portion 15. It will be appreciated that the peripheral edges of pre-cut overlay material 31 for the finger portions 16–19, as well as for the left side of thumb portion 15, will be positioned and affixed along the middle of the sides of the finger and thumb portions, respectively.

Figure 3:
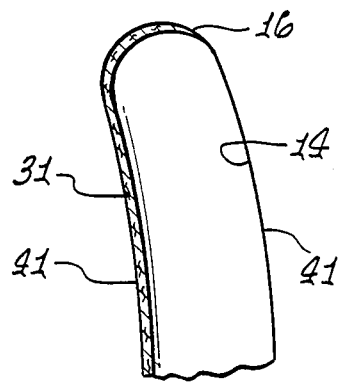
FIG. 3 is an enlarged cross-sectional view of the index or forefinger portion of the glove of FIG. 1 taken along the lines 3—3 as viewed from the right side of FIG. 1.

FIGS. 3 and 4 are enlarged sectional views of the index or forefinger portion 16 of glove 11. In these two views, the thickness of overlay material 31 is shown exaggerated for the purpose of illustration. The rear surface 14 of index finger portion 16 of glove 12 is identified, in FIGS. 3 and 4, as the inside surface, for reasons that will become apparent hereinafter. Overlay material 31 extends substantially to the tip of index finger portion 16, as seen in FIG. 3, and peripheral edges 34 and 35 of overlay 31 extend around the left and right sides to the positions shown in FIG. 4.

An acceptable surgical glove must be thin, pliable and tight-fitting to provide the required tactile sensitivity and ease of manipulation. It is necessary, therefore, for overlay material 31 of the improved surgical glove 11 to have a thinness and pliability approaching that of latex rubber. To achieve an improved penetration-resistant surgical glove, it is necessary to produce a special material having the required thinness and pliability as well as an additional toughness needed to prevent penetration by sharp-pointed instruments.

One representative example of a suitable material for overlay 31 is a special cloth obtainable from Burlington Industries, 1345 Avenue of the Americas, N.Y., N.Y. 10019, and having the specification listed below:
Material: High-density interwoven nylon yarn
Style No. 55116
Wieght: 1.5 ounces per square yard
Thickness: Approximately three-thousands (3/1000) of an inch
Type of Weave: Plain
Warp:
30 denier nylon yarn, duPont type 285, zero twist,
240 yarns per inch,
26 filaments per yarn,
Fill:
20 denier nylon yarn, duPont type 285, zero twist
200 yarns per inch
7 filaments per yarn
Color: White The high-density interwoven cloth identified above possesses a resistance to penetration by a sharp-pointed needle three to five times greater than that of latex rubber of the same thickness. Surgical glove 11, with its adhesively attached overlay material 31 composed of this special interwoven highdensity nylon, provides a resistance to penetration approximately five to seven times greater than the conventional surgeon's latex rubber glove.

The above-identified high-density nylon material forming overlay 31 is substantially non-elastic. Thus, while is possesses the desired thinness, i.e., three-thousandths of an inch, is extremely pliable and limp, it does not stretch. For this reason overlay material 31 is adhesively attached over only the front face or palmar surface 13 and partially around the left and right sides of thumb portion 15 and finger portions 16–19. The rear surface 14 of glove 11 and the sides of thumb portions 15 and finger portions 16–19 not covered by overlay 31 remain elastic, thereby enabling glove 11 to be readily fitted over the surgeon's hand.

The feel of improved surgical glove 11 upon the hand, thumb and fingers of the surgeon is substantially the same as the conventional latex rubber glove. By virtue of the nylon overlay material 31, the feel between the tip of thumb portion 15 and the tips of the finger portions 16–19 is different from that of latex rubber. Though somewhat subjective, this feel may be described as resembling, to some extent, the same feel as exists between the tips of the thumb and fingers of the surgeon when no glove is worn. The reason for this difference in feel is due to the differences between the surface texture of the high-density nylon overlay 31 and the surface texture of latex rubber.

By the simple expedient of reversing, i.e., turning surgical glove 11 inside out, it is apparent that the feel can be readily changed. A right-hand glove becomes a left-hand glove with overlay material 31 now located within glove 11. The feel between the tip of the thumb and the tips of the fingers of reversed glove 11 becomes that of latex rubber, the material of which foundation glove 12 is composed.

Without reversing, the feel of improved glove 11 can be made substantially the same as that to which the surgeon is accustomed by applying a thin over-coat of latex rubber. Thus is accomplished by dipping glove 11, while still mounted upon form 10, into a bath of liquid latex, withdrawing glove 11 with its form 10 from the bath of liquid latex, drying the thin coat of liquid latex adhering to the outer surface of glove 11, and curing the attached thin coat of latex by heating. This thin over-coat of latex rubber, identified by the numeral 41 as the outside surface of glove 11 in FIGS. 1-4, provides a hermetic seal over the entire outer surface of glove 11. Glove 11 now has an inside surface of latex rubber, i.e., foundation glove 12, and an outside surface of latex rubber, i.e., over-coat 41. Not only does latex over-coat 41 provide additional resistance to penetration, it also enhances the protection of both surgeon and patient from exposure to contamination.

In the event of a rupture or penetration of the hermetic seal provided by thin latex over-coat 41 covering front face 13 of glove 11, as might occur during the course of an operation, it has been observed that body liquids, such as blood, reaching overlay 31 will cause staining of overlay 31 which is visible through the semi-transparent, thin latex over-coat. This visual indication is of some importance to the operating surgeon and serves as a warning that may necessitate replacement of the glove whose hermetic seal has been compromised.

It will be appreciated that the high-density, tightly interwoven nylon cloth composed of a very large number of highstrength filaments above-identified is but one example of the type and nature of a class of polymer fibers or filaments suitable for overlay 31. An additional representative example is an interwoven material having a warp of 30 denier nylon yarn with 242 yarns per inch and a fill of 30 denier nylon yarn with 184 yarns per inch. This woven material, available from Burlington Industries and identified as Style No. 55163, consists of twenty-six (26) filaments per yarn in both the warp and the fill. While somewhat thicker, heavier, and less pliable, this woven material has excellent resistance to penetration. It is apparent, of course, that an overlay consisting of two or more layers of high-density, tightly interwoven, highstrength filaments will further enhance resistance to penetration, although sacrificing tactile sensitivity and ease of finger manipulation.

The twenty and thirty density yarns forming the nylon material of overlay 31 are composed of bundles of continuous filaments of high tensile strength. The cutting of overlay 31 in the shape of thumb 15, fingers 16–19, and palm portion 20 of glove 11 may expose the cut ends of the filaments in both the warp and the fill. To maintain the high tensile sterength inherent in each filament and to prevent sliding or slippage between adjacent filaments, the cut ends may be bonded on to the other by heat sealing. The preferred method by which heat sealing of the cut ends of the bundles of nylon filaments is accomplished is a process known as hot-knife sealing. This process achieves both cutting and sealing of the peripheral edges of overlay 31 by a simple procedure.

The improved surgical glove of the invention provides an appreciable improvement in resistance to penetration by sharp-pointed instruments, possesses a touch and feel closely approaching that of conventional surgical gloves, affords increased protection to both physician and patient, and produces a visual indication in the event of rupture or penetration.

Since many changes can be made in the above-described apparatus and many different embodiments of this invention could be made without departing from the scope thereof, it is intended that all matter contained in the above description or shown in the accompanying drawing shall be interpreted as illustrative and not in a limiting sense.

What is claimed is:

1. A penetration-resistance surgical glove comprising in combination:
   (a) a foundation glove composed of thin, resilient, elastic rubber having a front surface and a rear surface, said foundation glove including stalls for the thumb, fingers and palm of the human hand and a cuff for surrounding the wrist portion of the arm, said foundation glove providing a hermetic seal for covering the hand; and
   (b) an overlay of thin, pliable, limp and non-elastic material composed of a large number of tightly interwoven yarns of high strength, said overlay of thin, pliable, limp and non-elastic material being shaped to conform to the front surface of the thumb, fingers and palm portions of said foundation glove, said shaped overlay of thin, pliable, limp and non-elastic material being attached to the front surface of the thumb, fingers and palm portions of said foundation glove without rupture or penetration of the thin, resilient, elastic rubber forming said foundation glove, said overlay of thin, pliable, limp and non-elastic material having a thickness approximately equal to the thickness of the thin, resilient, elastic rubber forming said foundation glove and having a resistance to penetration by sharp-pointed instruments at least three times greater than the resistance to penetration of the thin, resilient, elastic rubber forming said foundation glove.

2. The penetration-resistance surgical glove as defined by claim 1 wherein said overlay of thin, pliable, limp and non-elastic material is composed of a large number of tightly interwoven yarns of polymer material, each of said yarns of polymer material being composed of bundles of high-strength polymer filaments.

3. The penetration-resistant surgical glove as defined by claim 1 wherein said overlay material composed of a large number of tightly interwoven yarns of high strength has a warp of at least two hundred yarns per inch, a fill of at least two hundred yarns per inch, and a thickness of from three- to four-thousandths of an inch.

4. The penetration-resistant surgical glove as defined by claim 1 wherein the tightly interwoven yarns of high strength of said overlay material are composed of at least seven filaments per yarn and wherein said overlay material has a weight of approximately one and one-half ounces per square yard.

5. A penetration-resistant surgical glove comprising in combination:
   (a) a foundation glove composed of thin, resilient, latex rubber having a front surface and a rear surface, said foundation glove including stalls for the thumb, fingers and palm of the human hand and a cuff for surrounding the wrist portion of the arm, said foundation glove providing a hermetic seal for covering the hand;
   (b) an overlay of thin, pliable, limp and non-elastic nylon cloth composed of a very large number of tightly interwoven nylon yarns of high strength, said tightly interwoven nylon yarns being composed of bundles of high-strength nylon filaments, said overlay of thin, pliable, limp and non-elastic nylon cloth including at least one hundred eighty yarns per inch in warp and at least one hundred eighty yarns per inch in fill, said overlay of thin, pliable, limp and non-elastic nylon cloth being cut and shaped to conform to the front surface of the thumb, fingers and palm portions of said foundation glove; and
   (c) means adhesively attaching said cut and shaped overlay of thin, pliable, limp and non-elastic nylon cloth to the front surface of the thumb, fingers and palm portions of said foundation glove without rupture or penetration of the thin, resilient, latex rubber forming said foundation glove, said overlay of thin, pliable, limp and nonelastic nylon cloth being especially resistant to penetration by sharp-pointed instruments.

6. The penetration-resistant surgical glove as defined by claim 5 further comprising a coat of thin, resilient, latex rubber covering said cut and shaped overlay of thin, pliable, limp and non-elastic nylon cloth adhesively attached to the front surface of the thumb, fingers and palm portions of said foundation glove, said coat of thin, resilient, latex rubber forming a hermetic seal over the surface of and around the edges of said adhesively attached cut and shaped overlay of thin, pliable, limp and non-elastic nylon cloth.

7. A penetration-resistant surgical glove comprising in combination:
   (a) a foundation glove composed of thin, resilient, elastic rubber having a front surface and a rear surface, said foundation glove including stalls for the thumb, fingers and palm of the human hand and a cuff for surrounding the wrist portion of the arm, said foundation glove providing a hermetic seal for covering the hand;
   (b) an overlay of thin, pliable, limp and non-elastic cloth material composed of a very large number of tightly interwoven polymer yarns of high strength, each of the polymer yarns of said overlay of cloth material having at least seven polymer filaments, said overlay of cloth material composed of a very large number of tightly interwoven polymer yarns having at least two hundred yarns per inch in warp and at least two hundred yarns per inch in fill, said overlay of thin, pliable, limp and non-elastic cloth material having a thickness of approximately three- to four-thousandths of an inch, said overlay of thin, pliable, limp and non-elastic cloth material being cut and shaped to conform to the front surface of the thumb, finger and palm portions of said foundation glove; and (c) means attaching said cut and shaped overlay of cloth material to the front surface of the thumb, fingers and palm portions of said foundation glove without rupture or penetration of the thin, resilient, elastic rubber forming said foundation gloove, the combination penetrationresistant surgical globe having a resistance to peentration by sharp-pointed needles at least five times greater than the resistance to penetration of said foundation glove.

8. The penetration-resistant surgical glove as defined by claim 7 further comprising a coat of thin, resilient, elastic rubber covering said cut and shaped overlay of thin, pliable, limp and non-elastic cloth material attached to the front surface of the thumb, fingers and palm portions of said foundation glove, said coat of thin, resilient, elastic rubber forming a hermetic seal over the surface of and around the edges of said attached cut and shaped overlay of thin, pliable, limp and non-elastic cloth material.

* * * * *